United States Patent
Shinohara et al.

(10) Patent No.: US 7,341,857 B2
(45) Date of Patent: Mar. 11, 2008

(54) **PRODUCTION OF BETA-HYDROXYPALMITATE METHYL ESTERASE FROM *IDEONELLA* SP.0-0013 (FERM BP-08660)**

(75) Inventors: Makoto Shinohara, Aichi (JP); Yoichi Uehara, Aichi (JP); Akimasa Nakano, Aichi (JP)

(73) Assignee: Incorporated Administrative Agency National Agriculture and Bio-Oriented Research Organization, Tsukuba-shi (JP)

( * ) Notice: Subject to any disclaimer, the term of this patent is extended or adjusted under 35 U.S.C. 154(b) by 338 days.

(21) Appl. No.: 10/548,872

(22) PCT Filed: Mar. 16, 2004

(86) PCT No.: PCT/JP2004/003472

§ 371 (c)(1),
(2), (4) Date: Sep. 14, 2005

(87) PCT Pub. No.: WO2004/083420

PCT Pub. Date: Sep. 30, 2004

(65) Prior Publication Data

US 2006/0194295 A1    Aug. 31, 2006

(30) Foreign Application Priority Data

Mar. 17, 2003    (JP) ............................... 2003-071376

(51) Int. Cl.
C12N 9/20    (2006.01)
C12N 1/12    (2006.01)
C12N 1/20    (2006.01)
C12P 7/64    (2006.01)

(52) U.S. Cl. .................... 435/198; 435/134; 435/252.1
(58) Field of Classification Search .................... None
See application file for complete search history.

(56) References Cited

FOREIGN PATENT DOCUMENTS

| JP | 11-56349 | 3/1999 |
|---|---|---|
| JP | 11-56364 | 3/1999 |

OTHER PUBLICATIONS

Shinohara et al. (2007) Purification and characterization of a novel esterase (B-hydroxypalmitate methyl ester hydrolase) and prevention of the expression of virulence by Ralstonia solanacearum. J. Appl. Microbiol. 103:152-162.*
Macrae, A. (2000) The Use of 16S rDNA Methods is Soil Microbial Ecology. Brazilian J. Microbiol. 31:77-82.*

* cited by examiner

*Primary Examiner*—Lisa J Hobbs
(74) *Attorney, Agent, or Firm*—Antonelli, Terry, Stout & Kraus, LLP.

(57) ABSTRACT

The present invention provides a novel esterase derived from *Ideonella* sp. 0-0013 strain (FERM BP-08660) having the following properties: (1) function, substrate specificity: hydrolyzes methyl 3-hydroxypalmitate to generate 3-hydroxypalmitic acid and methanol; (2) optimal temperature for functioning: 37° C.; (3) optimal pH and stable pH range: pH 7 or more to pH 10 or less; (4) temperature stability: 97% of the enzyme is stable at 43° C.; (5) inhibition, activation, and stabilization: activated by sodium ion and potassium ion, and inhibited by strontium ion, iron ion (divalent), and methyl palmitate; (6) molecular weight: about 46,500 Da (by SDS-PAGE), about 41,000 Da (by a gel filtration method); and (7) isoelectric point: pI 4 (by polyacrylamide gel isoelectric focusing method); a microorganism producing the enzyme; and a method of producing the enzyme.

3 Claims, No Drawings

PRODUCTION OF BETA-HYDROXYPALMITATE METHYL ESTERASE FROM *IDEONELLA* SP.0-0013 (FERM BP-08660)

TECHNICAL FIELD

The present invention relates to a novel esterase, a microorganism producing said enzyme and a method of producing said enzyme. This enzyme has an effect of restraining pathogenic expression of *Ralstonia solanacearum*.

BACKGROUND ART

Bacterial wilt, which brings down serious damages to agricultural crops, is known to be a disease that is dif posed of a single subunit judging from the value of its molecular weight. This enzyme can be obtained by cultivating *Ideonella* sp. 0-0013 strain in a medium. The *Ideonella* sp. 0-0013 strain, a novel esterase-producing microorganism, was isolated from the soil collected in Aichi by the inventors of the present invention. More specifically, the strain was isolated using an isolation medium that contains methyl 3-hydroxypalmitate as a single carbon source.

This microorganism was identified to belong to the genus *Ideonella* by analyzing the entire base sequence of 16S rDNA. The results are as follows.

When the base sequence of 16S rDNA of 1,158 bp was determined and BLAST search was performed, it revealed that the strain of the present invention had a high homology with microorganisms belonging to the genus *Ideonella*, with a 99% homology with the *Ideonella* sp. B513 strain (a strain derived from a rice plant) and the like and with a 98% homology with *Ideonella dechloratans*.

From the above-mentioned results, the *Ideonella* sp. strain of the present invention isolated from the soil as having a high activity to hydrolyze methyl 3-hydroxypalmitate was identified as the *Ideonella* sp.

The mycological properties of the strain of the present invention are as follows.

The strain grows well at 30 to 43° C. on Nissui standard medium (manufactured by Nissui Pharmaceutical) to form white colonies. It also grows on an LB medium but slightly poorly. On an agar medium containing methyl 3-hydroxypalmitate as a single carbon source, it grows at 43° C. It does not grow well on agar media that contain methyl palmitate or methanol as a single carbon source, respectively.

The *Ideonella* sp. Strain of the present invention was recognized by 16S rDNA sequencing to be a new species and deposited under the Budapest Treaty on Mar. 12, 2003 at the International Patent Organism Depositary, National Institute of Advanced Industrial Science and Technology at Tsukuba Central 6, 1-1, Higashi 1-Chome, Tsukuba-shi, Ibaraki-ken, Japan with an Accession Number: FERM BP-08660 (transferred from FERM P-19248). As described by 37 CFR 1.808, upon granting of the patent, all restrictions imposed by the depositor, subject to paragraph (b), on the availability to the public of the deposited material will be irrevocably removed for the term of the patent. In the present invention, those variants that are obtained by mutating the strain of the present invention naturally or with artificial means can also be used as far as they have an ability to produce the target esterase.

The microorganisms that produce the novel enzyme of the present invention that can be used include besides the above strain of the present invention, genetically engineered microorganisms or plants obtained by incorporating an enzyme gene isolated from the strain of the present invention into various host vector systems.

As the enzyme described in claim 1, the culture broths obtained by cultivating the above-mentioned microorganisms or the like in a medium can be used as they are. Alternatively, supernatants or microbial cells recovered from the culture broths, or their treated products can be used as a crude enzyme.

The treated microbial cells include, for example, crushed microbial cells, cell-free extracts obtained by crushing microbial cells, and microbial cells treated with organic solvents such as acetone, toluene, etc. Examples of the enzyme that can be used include in addition to those described above, a crude enzyme or a purified enzyme separated from the microbial cells, immobilized microbial cells or immobilized enzyme.

When using the enzyme, it is convenient to immobilize the enzyme to an appropriate carrier before it can be used. This facilitates separation and recovery of the enzyme from the reaction mixture after completion of the reaction and also reuse of the enzyme. Examples of the carrier that can be used include polyacrylamide and hydroxyapatite.

In the present invention, usually one kind of the crude enzyme such as microbial cells culture broth, microbial cells, or treated microbial cells or a purified enzyme can be used. However, two or more kinds having similar abilities can be used in combination as desired.

Any medium can be used as the medium for cultivating the above-mentioned microorganisms as far as the microorganism can grow. Preferable examples of the medium include Nissui Standard Medium (manufactured by Nissui Pharmaceutical), and SCD medium (manufactured by Nihon Pharmaceutical). The microorganisms can grow well in these medium. To obtain higher enzyme activities, it is effective to add compounds having skeleton of ester of fatty acid such as methyl 3-hydroxypalmitate and methyl palmitate to the medium and utilize the compounds as an induction substance for producing the enzyme.

Cultivation can be performed by a conventional method. For example, cultivation is performed at pH 4 to 10, preferably 6 to 8, at a temperature in the range of 15 to 50° C., preferably 30 to 45° C., for 6 to 96 hours, preferably 12 to 30 hours aerobically. Sometimes, a higher enzyme activity can be obtained by stationary culture in a similar manner.

After completion of the cultivation, when the enzyme is separated and collected from the culture broth, and purified, a conventional method may be followed. For example, the enzyme can be purified from: a supernatant obtained by a solid-liquid separating means such as centrifugation, from the culture broth; a cell-free extract obtained by crushing the microbial cells; or an extract with solvent such as acetone, toluene, etc., by a conventional method such as concentration, filtration, or chromatography, etc.

The esterase of the present invention has the following properties.

(1) Function, substrate specificity: Hydrolyzes methyl 3-hydroxypalmitate to generate 3-hydroxypalmitic acid and methanol.

Methyl 3-hydroxypalmitate is detected by gas chromatography with a column of Stabilwax-DA, 30 m×0.53 mm×0.25 µm. The 3-hydroxypalmitic acid generated by hydrolysis of the ester can be detected by the same gas chromatography as described above.

(2) Optimal temperature for functioning: The optimal temperature of the enzyme of the present invention is 37° C.

(3) Optimal pH and stable pH range: pH 7 or more to pH 10 or less.

(4) Temperature stability: 97% of the enzyme is stable at 43° C., 54% of the enzyme is stable at 50° C., and 38% of the enzyme is stable at 60° C.

(5) Inhibition, activation, and stabilization: Activated by sodium ion and potassium ion, and inhibited by strontium ion, iron ion (divalent), and methyl palmitate.

(6) Molecular weight: About 46,500 Da (by SDS-PAGE), about 41,000 Da (by a gel filtration method).

(7) Isoelectric point: pI 4 (by polyacrylamide gel isoelectric focusing method).

Hereinafter, the present invention is explained in more detail by way of examples. However, the present invention is not limited by them.

EXAMPLE 1

200 mL of a medium containing 2.5 g/L yeast extract, 5.0 g/L peptone, and 1.0 g/L glucose was dispensed in a 500-mL Erlenmeyer flask and heated at 121° C. for 25 minutes to sterilize it. Then the *Ideonella* sp. 0-0013 strain (FERM BP-08660) was inoculated and cultivated with shaking at 43° C. for 20 hours.

After completion of the cultivation, the culture broth was centrifuged to obtain a supernatant, which was used as a crude enzyme. For purifying the enzyme, 70% ammonium sulfate fractionation was performed.

TEST EXAMPLE 1

The culture broth obtained by cultivating the strain in the same manner as that in Example 1 was centrifuged to obtain a supernatant and microbial cells. The supernatant or the microbial cells were suspended in 200 μL of 10 mM potassium phosphate buffer (pH 7.0) containing 0.5 mg of methyl 3-hydroxypalmitate, and the resultant was allowed to react at 43° C. for 12 hours.

After completion of the reaction, 500 μL of dichloromethane was added to the reaction mixture to extract 3-hydroxypalmitic acid. The extract was subjected to gas chromatography (Stabilwax-DA, 30 m×0.53 mm×0.25 μm) to measure the decomposing activity of methyl 3-hydroxypalmitate. The results obtained are shown in Table 1.

TABLE 1

| Operation | Concentration of methyl 3-hydroxypalmitate (mmol/L) | Concentration of 3-hydroxypalmitic acid (mmol/L) | Decomposition (%) |
|---|---|---|---|
| Control | 6.07 | Not detected | — |
| Supernatant | 0.06 | 1.81 | 99 |
| Microbial cell | 1.43 | Not detected | 76 |

TEST EXAMPLE 2

0.5 mg of methyl palmitate or methyl 3-hydroxypalmitate was reacted and analyzed in the same manner as that in Example 1 and the decomposing activities of the compounds were measured in each case. The results obtained are shown in Table 2.

TABLE 2

|  | Decomposition (%) | Activity ratio |
|---|---|---|
| Methyl 3-hydroxypalmitate | 50.3 | 100.0 |
| Methyl palmitate | 10.3 | 20.5 |

The table shows that the hydrolytic activity for methyl 3-hydroxypalmitate is about 5 times as high as that for methyl palmitate. This indicates that the enzyme activity of the present invention is selective to methyl 3-hydroxypalmitate.

INDUSTRIAL APPLICABILITY

According to the present invention, an enzyme that hydrolyzes methyl 3-hydroxypalmitate is provided. Methyl 3-hydroxypalmitate acts as a regulator for the expression of pathogenicity in *Ralstonia solanacearum*. The enzyme of the present invention that hydrolyzes said compound is useful for effectively restraining bacterial wilt.

What is claimed is:

1. An isolated esterase obtained from *Ideonella* sp. 0-0013 strain (FERM BP-08660) having the following properties:
   (1) Function, substrate specificity: hydrolyzes methyl 3-hydroxypalmitate to generate 3-hydroxypalmitic acid and methanol;
   (2) Optimal temperature for functioning: 37° C.;
   (3) Optimal pH and stable pH range: pH 7 or more to pH 10 or less;
   (4) Temperature stability: 97% of the enzyme is stable at 43° C.;
   (5) Inhibition, activation, and stabilization: Activated by sodium ion and potassium ion, and inhibited by strontium ion, iron ion (divalent), and methyl palmitate;
   (6) Molecular weight: About 46,500 Da (by SDS-PAGE), about 41,000 Da (by a gel filtration method); and
   (7) Isoelectric point: pI 4 (by polyacrylamide gel isoelectric focusing method).

2. A biologically pure culture of *Ideonella* sp. 0-0013 strain (FERM BP-08660) having an ability to produce an enzyme that hydrolyzes methyl 3-hydroxypalmitate to generate 3-hydroxypalmitic acid and methanol.

3. A method of producing an esterase of claim 1, comprising:
   cultivating *Ideonella* sp. 0-0013 strain (FERM BP-08660) in a medium; and
   collecting said esterase from culture broth.

* * * * *